United States Patent
Zhou et al.

(10) Patent No.: US 10,952,699 B2
(45) Date of Patent: Mar. 23, 2021

(54) AUTOMATED BLOOD POOL IDENTIFICATION SYSTEM AND METHOD OF OPERATION THEREOF

(71) Applicant: KONINKLIJKE PHILIPS N.V., Eindhoven (NL)

(72) Inventors: Shiwei Zhou, Acton, MA (US); Balasundar Iyyavu Raju, North Andover, MA (US); Shougang Wang, Ossining, NY (US); Jingping Xu, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 325 days.

(21) Appl. No.: 16/061,425

(22) PCT Filed: Dec. 30, 2016

(86) PCT No.: PCT/EP2016/082944
§ 371 (c)(1),
(2) Date: Jun. 12, 2018

(87) PCT Pub. No.: WO2017/114961
PCT Pub. Date: Jul. 6, 2017

(65) Prior Publication Data
US 2020/0268343 A1    Aug. 27, 2020

Related U.S. Application Data

(60) Provisional application No. 62/273,699, filed on Dec. 31, 2015.

(51) Int. Cl.
*A61B 8/08* (2006.01)
*A61B 8/00* (2006.01)
*A61B 5/02* (2006.01)

(52) U.S. Cl.
CPC .............. *A61B 8/085* (2013.01); *A61B 8/461* (2013.01); *A61B 8/469* (2013.01); *A61B 8/5223* (2013.01);
(Continued)

(58) Field of Classification Search
CPC ....... A61B 8/085; A61B 8/461; A61B 8/5223; A61B 8/5238; A61B 8/54; A61B 8/469; A61B 5/02042; A61B 8/4444
See application file for complete search history.

(56) References Cited

U.S. PATENT DOCUMENTS 5,487,387 A    1/1996    Trahey et al.
2010/0331698 A1    12/2010    Tonomura
(Continued)

FOREIGN PATENT DOCUMENTS

WO    2009104525 A1    6/2011
WO    2014136018 A1    9/2014
(Continued)

OTHER PUBLICATIONS

K. Markus et.al, 'Current role of emergency US in patients with major trauma', RadioGraphics, 2008, vol. 28: 225-291.
(Continued)

*Primary Examiner* — Wesley J Tucker

(57) ABSTRACT

An ultrasound imaging apparatus (200, 600) may include at least one controller (210, 610) which may be configured to: acquire ultrasound data of an anatomical region-of-interest (ROI), the ultrasound data including at least two frames acquired at different times over an interval of time as a push force is applied to induce movement in the anatomical ROI; determine a correlation between at least two of the acquired frames and form corresponding correlation coefficients; generate a correlation coefficient (CC) map based upon the determined correlation information between the at least two
(Continued)

frames; and distinguish fluid from tissue within the CC map based upon a comparison of the correlation coefficients with at least one threshold value.

20 Claims, 4 Drawing Sheets

(52) U.S. Cl.
CPC .............. *A61B 8/5238* (2013.01); *A61B 8/54* (2013.01); *A61B 5/02042* (2013.01); *A61B 8/4444* (2013.01)

(56) References Cited

U.S. PATENT DOCUMENTS

| | | | |
|---|---|---|---|
| 2015/0141821 A1 | 5/2015 | Yoshikawa et al. | |
| 2016/0000398 A1* | 1/2016 | Raju | A61B 8/14 600/443 |
| 2017/0273658 A1* | 9/2017 | Wang | A61B 8/06 |
| 2018/0303459 A1* | 10/2018 | Walton | A61B 8/06 |
| 2019/0125310 A1* | 5/2019 | Takeda | A61B 8/5207 |
| 2020/0022671 A1* | 1/2020 | Noguchi | A61B 8/5276 |

FOREIGN PATENT DOCUMENTS

| | | | | |
|---|---|---|---|---|
| WO | WO-2014136018 A1 * | 9/2014 | ......... | G01S 7/52042 |
| WO | 2014162966 A1 | 2/2017 | | |

OTHER PUBLICATIONS

C.H. Kim et al., 'Diagnostic Acuuracy of Focused Assessment with Sonography for Trauma (FAST) Examinations Performed by Emergency Medical Technicians', Pre-hospital Emergency Care, 2012, vol. 16, No. 3: pp. 400-406.

"Signal Processing: Continuous and Discrete" MIT Open Course Ware, Fall, 2008.

* cited by examiner

AUTOMATED BLOOD POOL IDENTIFICATION SYSTEM AND METHOD OF OPERATION THEREOF

This application is the U.S. National Phase application under 35 U.S.C. § 371 of International Application No. PCT/EP2016/082944, filed on Dec. 30, 2016, which claims the benefit U.S. Provisional Application Ser. No. 62/273, 699, filed Dec. 31, 2015. These applications are hereby incorporated by reference herein.

The present system relates to an automated ultrasound blood pool detection (BPD) system and, more particularly, to an automated low-energy ultrasound BPD system which employs low-energy induced movements to obtain data de-correlation patterns to detect blood pools, and a method of operation thereof.

Trauma is a serious public health problem with significant social and economic costs. Typically, abdominal trauma can injure organs such as the liver, the kidney and the spleen, which injury can lead to a collection of free blood in the peritoneal space of injured persons. This collection of free blood in the peritoneal space is undesirable and can be detected using ultrasound imaging methods which may employ a FAST protocol (Focused Assessment with Sonography in Trauma) in which an ultrasound probe is placed at four different locations on the body (e.g., abdomen, chest) of the injured person to collect ultrasound image information which is then displayed. A user, such as a clinician, must then visually observe the displayed ultrasound image information to detect a presence of free blood by identifying hypoechoic regions. Unfortunately, when using conventional imaging methods such as the FAST imaging method discussed above, it is difficult for inexperienced users (e.g., clinicians) to accurately detect blood pools due to the sensitivity of ultrasound imaging systems and methods. Moreover, the above-described process is time consuming and accuracy is heavily dependent on operator experience.

Accordingly, embodiments of the present system may overcome these and other disadvantages of conventional registration systems.

The system(s), device(s), method(s), arrangements(s), user interface(s), computer program(s), processes, etc. (hereinafter each of which will be referred to as system, unless the context indicates otherwise), described herein address problems in prior art systems.

In accordance with embodiments of the present system, there is disclosed an ultrasound imaging apparatus which may include: at least one controller configured to: acquire ultrasound data of an anatomical region-of-interest (ROI) of a subject, the ultrasound image information including at least two frames (e.g. a current frame and a selected previous frame, if desired) acquired at different times over as a push force induces movement within the anatomical ROI; determine a correlation between at least two of the acquired frames and form corresponding correlation coefficients; generate a correlation coefficient (CC) map based upon the determined correlation information between the at least two frames; and/or distinguish fluid from tissue within the CC map based upon a comparison of the correlation coefficients with at least one threshold value.

The at least one controller may be further configured to highlight the fluid within the CC map. Further, during the comparison, it is envisioned that the at least one controller may determine whether the correlation coefficients are less than at least one threshold value. Then, when the correlation coefficients are determined to be less than a threshold value, the at least one controller marks a corresponding area on the CC map as a fluid area. Conversely, when the correlation coefficients are determined to be not less than the threshold value, the at least one controller marks a corresponding area on the CC map as a tissue area. It is further envisioned that the system may include an actuator to generate a push force to be coupled to the ROI under the control of the at least one controller. It is envisioned that the actuator may be an ultrasound actuator and the push force may be a low-energy ultrasound pulse.

In accordance with yet other embodiments of the present system, there is disclosed a method of displaying ultrasound images, the method performed by at least one controller of an imaging system and may include acts of: acquiring ultrasound image information of an anatomical object within a region-of-interest (ROI), the ultrasound image information including at least two consecutive frames acquired at different times over an interval of time as a push force is applied to the anatomical object; determining a correlation between at least two of the acquired frames and forming corresponding correlation coefficients; generating a correlation coefficient (CC) map based upon the determined correlation information between the at least two frames; and/or distinguishing fluid from tissue within the CC map based upon a comparison of the correlation coefficients with a threshold value.

The method may further include an act of highlighting the fluid within the CC map. Further, during the act of comparing, it may be determined whether the correlation coefficients are less than a threshold value. Then, when the correlation coefficients are determined to be less than the threshold value, a corresponding area on the CC map is marked as a fluid area. Conversely, when the correlation coefficients are determined to be not less than the threshold value, a corresponding area on the CC map is marked as a tissue area. The method may further include an act of generating a push force to be coupled to the ROI. This push force may be a low-energy ultrasound pulse generated by a low-energy ultrasound actuator.

In accordance with embodiments of the present system, there is further disclosed a non-transitory computer readable medium including computer instructions which, when executed by a processor, configure the processor to perform the acts of and/or to cause performance of acts of: acquiring ultrasound image information of an anatomical object within a region-of-interest (ROI), the ultrasound image information including at least two consecutive frames acquired at different times over an interval of time as a push force is applied to the anatomical object; determining a correlation between at least two of the acquired frames and forming corresponding correlation coefficients; generating a correlation coefficient (CC) map based upon the determined correlation information between the at least two frames; and/or distinguishing fluid from tissue within the CC map based upon a comparison of the correlation coefficients with a threshold value. It is further envisioned that the method may include an act of highlighting the fluid within the CC map. Moreover, during the act of comparing, it may be determined whether the correlation coefficients are less than a threshold value. Accordingly, when the correlation coefficients are determined to be less than the threshold value, a corresponding area on the CC map may be marked as a fluid area; and when the correlation coefficients are determined to be not less than the threshold value, a corresponding area on the CC map may be marked as a tissue area. The computer instructions may further configure the processor to cause generation of a push force to be coupled to the ROI during the acquisition, such as by controlling a low-energy ultrasound actuator to generate a low-energy ultrasound pulse.

The present invention is explained in further detail in the following exemplary embodiments and with reference to the figures, where identical or similar elements are partly indicated by the same or similar reference numerals, and the features of various exemplary embodiments being combinable. In the drawings.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements. The term and/or and formatives thereof should be understood to mean that only one or more of the recited elements may need to be suitably present (e.g., only one recited element is present, two of the recited elements may be present, etc., up to all of the recited elements may be present) in a system in accordance with the claims recitation and in accordance with one or more embodiments of the present system.

Figure 1:
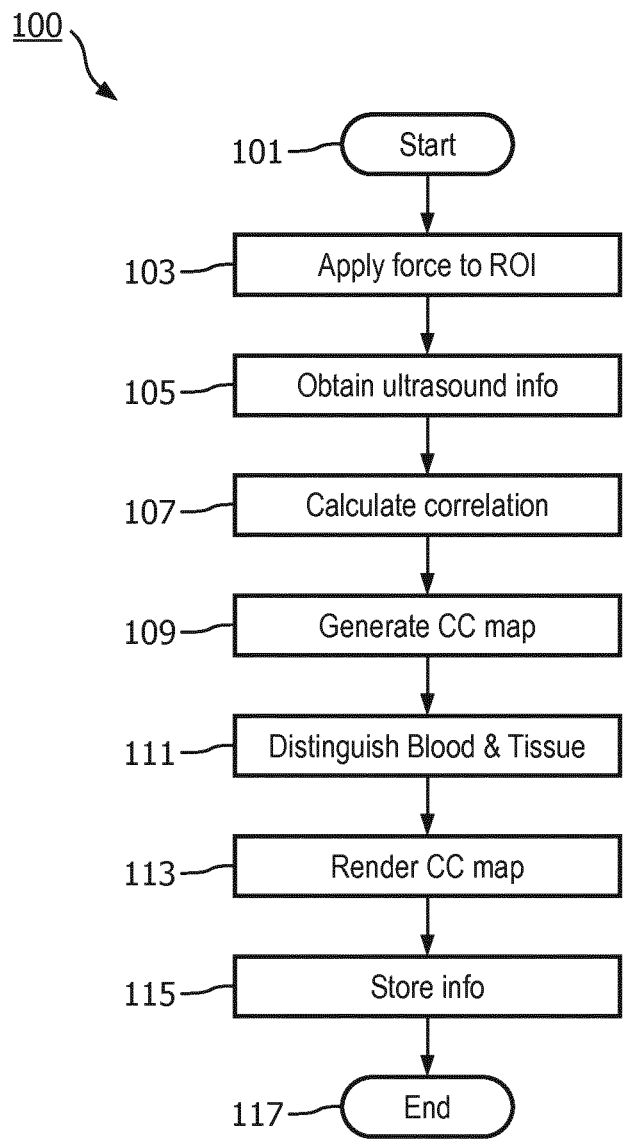
FIG. 1 shows a flow diagram that illustrates a process performed by a system in accordance with embodiments of the present system.

FIG. 1 shows a flow diagram that illustrates a process 100 performed by a system in accordance with embodiments of the present system. The process 100 may be performed using one or more computers communicating over a network and may obtain information from, and/or store information to, one or more memories of the system which may be local and/or remote from each other. The process 100 can include one of more of the following acts. Further, one or more of these acts may be combined and/or separated into sub-acts, if desired. Further, one or more of these acts may be skipped depending upon settings.

In certain embodiments, systems and methods of the invention are performed on an ultrasound imaging apparatus configured to control one or more transducer arrays to transmit ultrasound waves and receive echoes for generating ultrasound images based on the echoes. The ultrasound imaging apparatus may include processors, beamformers, and other circuitry as needed for signal processing and image generation. The transducer arrays may be incorporated configured to generate 1D, 2D, and/or 3D images. The transducer arrays may be incorporated into a probe, patch, or other configuration. The ultrasound imaging system may be operable for imaging in a variety of different modalities (e.g., B-mode, M-mode, PW Doppler, spectral Doppler, etc.). For example, the imaging apparatus may be an ultrasound imaging system implemented on a hand-held device (e.g., tablet, smartphone, etc.) such as the VISIQ or LUMIFY ultrasound systems provided by PHILIPS). In some examples, the imaging apparatus may be an ultrasound imaging system implemented in a more conventional form factor, e.g., as larger but still typically portable base, which may provide a variety of imaging functions (e.g., B-mode, M-mode, color flow Doppler, PW Doppler, spectral Doppler, and other ultrasound imaging modes). For example, the imaging apparatus may be an ultrasound imaging system such as the SPARQ or EPIQ ultrasound systems provided by PHILIPS. Other ultrasound systems may be used.

In operation, the process may start during act 101 and then proceed to act 103.

During act 103, the system may apply an optional force to a region-of-interest (ROI) of a subject so as to impart movement to the ROI. The force may be applied externally (e.g. due to an external force applied to a subject that imparts movement to the internal ROI) or internally (e.g. due to an internal force original from within the subject that imparts movement to the ROI, such as breathing). This force may be referred to as a displacement force or a push force.

According to certain aspects, the system may be operative to drive any suitable actuator (such as a transducer, an electromechanical actuator, etc.) to generate the displacement force so as to impart movement within a volume of the ROI. The system may drive the source at a desired frequency and/or amplitude which may be lower than a respective frequency and/or amplitude of a push force generated by acoustic streaming methods. Further, the source may include an ultrasound probe which may be driven to generate pulses (e.g., periodic and/or non-periodic) which may have lower energy than ultrasound pulses used for acoustic streaming methods. These pulses may be used as the displacement force. Regardless of whether the displacement forces are formed by an ultrasound probe or mechanical actuator, the system may be operative without the need for high intensity pulses which are required by acoustic streaming methods.

However, in yet other embodiments, the system may rely upon external and/or internal actuators and/or other sources (e.g., actuators or biological sources) to provide the displacement force so as to impart movement to the object under test (such as a patient, a phantom, etc.) within the anatomical ROI. For example, the force may be generated internally (e.g., a force due to breathing, etc.) by a patient under observation. For example, the blood mostly resides between internal organs such as the Morrison's porch between liver and kidney. As the organs moves as part of the inherent body motion mainly caused by breathing, they push and squeezes the blood as well. Additionally, the force may be applied (e.g., by tapping, pressing, squeezing, etc.) at or adjacent to the ROI by a user (e.g., a clinician, etc.).

The source employed by the system may be dependent upon a location of the ROI. For example, if the ROI is within a body cavity such as the abdomen, the system may determine to use an internal source (e.g., a force of breathing generated by the patient) rather than applying a force generated by the system and/or clinician. However, if the ROI is outside of body cavity such as at an arm, a leg, etc., then the system may be operative to control a source of the system such as an actuator to apply a force to the ROI. Accordingly, the system may determine a location of the ROI and determine whether to actuate a source of the system based upon the determination (e.g., if the ROI is an abdomen (e.g., for an abdomen scan), then use internal source; and if the ROI is a limb (e.g., for a limb scan), then use an external source). Thus, the system may determine whether to use and/or drive a system source based upon a type of scan (e.g., abdomen scan, limb scan, etc.) being performed.

Once motion has been imparted to the ROI (either externally or internally), systems and methods of the invention provide for obtaining ultrasound data of the ROI in order to track and correlate the movement across a period of time. The system may determine the type of scan being performed using any suitable method such as by identifying a user's selection (e.g. perform cavity scan, neck scan, etc.). In certain embodiments, the system may activate a source based upon a selection of the user (e.g. use external source rather than internal source). During a scan, sensors of the system (e.g., accelerometers, force sensors, etc. within a probe) may detect a force being applied, form corresponding sensor information, and provide the sensor information to a controller of the system for further analysis. The controller may then determine whether the force being applied (during a scan) is sufficient (e.g., by comparison with a force threshold or thresholds stored in a memory of the system) and when it is determined that the force is not sufficient (i.e., insufficient), the controller may inform the user of such. This may prevent erroneous data collection when the clinician is the source.

Moreover, the system may output instructions (e.g., via a display, a speaker, etc.) to a user on how (e.g., by tapping the ROI) and/or when to apply a force, if desired. Further, the system may output these instructions when it is determined that the force is insufficient during a scan as discussed above.

In accordance with embodiments of the present system, the system may determine whether to drive the source based upon a selection of a user (e.g., use internal source or use external source (e.g., system or user)), which user selection may be entered in real time and/or stored in a memory of the system for later use. After completing act 103, the process may continue to act 105.

During act 105, the system may obtain ultrasound image information from the ROI. Accordingly, the system may drive an ultrasound transducer near and/or coupled to the ROI and receive (e.g., via receivers of the ultrasound transducer) corresponding ultrasound image information from the ROI. The ROI may be within an anatomical object or subject such as a human, an animal, a phantom (e.g., for testing), etc. The ultrasound information may then be processed into any suitable desired format such as raw radiofrequency (RF) data, Digital Imaging and Communications in Medicine (DICOM) data, or the like (hereinafter both of which may be referred to as collected ultrasound information unless the context indicates otherwise for the sake of clarity). Accordingly, the ultrasound image information may include collected raw RF data and/or digital ultrasound information such as DICOM data. The ultrasound information may be collected over an interval of time (e.g., 1, 2, 3, 4, or 5 second intervals, although other time intervals are also envisioned) at a suitable frame rate such as a normal imaging frame rate (e.g., 30 frames per second, although other frame rates are also envisioned). Thus, the collected information may include a plurality of ultrasound image frames (hereinafter referred to as frames for the sake of clarity unless the context indicates otherwise) over a selected time interval. The ultrasound transducer may include any suitable ultrasound transducer such as a multichannel transducer array. However, in yet other embodiments, the ultrasound information may be obtained from a memory of the system (e.g., stored ultrasound information). After completing act 105, the process may continue to act 107.

The ultrasound data collected from the ROI can then be used to distinguish between tissue and blood During act 107, the system may calculate a 1D or 2D correlation or cross-correlation (generally, the correlation) between two or more frames of the collected ultrasound information. For example, discrete-time signals of two or more frames of the RIO may be captured and cross-correlated, and a correlation coefficient is calculated. In certain embodiments, the two or more frames are consecutive. In other embodiments, the two or more frames are spaced apart in a pre-defined period of time. The correlation may be performed by any suitable application and/or algorithm well known in the art. For example, using techniques described in Proakis and Manolakis, Digital Signal Processing, 4th Edition, Pearson 2007, Oppenheim, Alan V., and Ronald W. Schafer. Discrete-time signal processing. Pearson Higher Education, 2010; and MIT OpenCourseWare, 2.161 Signal processing: Continuous and Discrete, https://ocw.mitedu/courses/mechanical-engineering/2-161-signal-processing-continuous-and-discrete-fall-2008/lecture-notes/lecture_22.pdf (Fall 2008). In certain embodiments, correlation coefficients between frames may be determined by using existing multiply and sum correlation methods to assess lags or differences between two or more signals of frames. These methods can be applied at one or more signals between two frames (e.g. one or more corresponding signals from each frame), and the result is a correlation signal as a function of lag. In one embodiment, one or more signals from a frame may be compared to one or more signals from another frame. In another embodiment, one or more plurality of signals from a frame may be compared to one or more plurality of signals from another frame ((e.g. signals within a segmented window of a frame may be compared to signals within a segmented window of another frame).

Generally, the correlation establishes a relationship of one or more objects between two or more frames. Solids (like tissue, bone, etc.) tend to move in unison in response to a force, and thus signals emitted from solids tend to be strongly correlated—i.e. match well when signals are aligned. Typically, correlation coefficients for solids across frames are about 0.9 or greater, but may be in the range of 0.8 or greater. Whereas, the movement of fluids (blood, plasma, water, etc.) tends to be non-unison (more scattered) in response to a force, and thus the signals emitted from the signals tend to be less strongly correlated. Typically, correlation coefficients for fluids across frames are about 0.8 or lower, but may be in the range of 0.9 or lower. As such, there may be an intermediate correlation coefficient zone of about 0.8-0.9 in which the signals are indicative of tissue and/or fluid.

Systems and methods of the invention may provide threshold correlation coefficients for tissues, fluids, and/or intermediate objects. The calculated correlation coefficients for signals across two or more frames may be compared to the threshold correlation coefficients, and the system may use the comparison to identify the objects within the frames as tissue, fluid, and/or indeterminate. One or more of these determinations may be conducted prior to or after generation of the correlation coefficient map (act 109). In certain embodiments, a single correlation coefficient threshold is used to differentiate solid and fluids in the imaging data, and the single correlation coefficient threshold may be about 0.80, 0.81, 0.82, 0.83 . . . , 0.90, or 0.91. In other embodiments, there may be a tissue correlation coefficient threshold separate from a fluid correlation coefficient threshold, in which a) calculated correlation coefficients above the tissue correlation coefficient threshold may be identified as tissue, b) calculated correlation coefficients below the fluid correlation coefficient threshold may be identified as fluid. The tissue correlation coefficient threshold may be, for example, 0.85, 0.86 . . . , 0.90, 0.91. The fluid correlation coefficient threshold may be, for example, 0.79, 0.80, . . . , 0.84, 0.85. In some instances, objects having a correlation coefficient value between the fluid and tissue coefficient thresholds may be identified as indeterminable to the operator such that further investigation into object-type may be conducted.

After completing act 107, the process may continue to act 109.

During act 109, the system may generate a correlation coefficient (CC) map in accordance with the collected ultrasound information. The CC map may indicate different extents of correlation and de-correlation (e.g., frame to frame), and hence different motion patterns between blood and surrounding soft tissues. For the sake of clarity, it will be assumed that as the correlation decreases, the de-correlation increases.

In some instances, the system may distinguish between blood and surrounding soft tissue based upon the CC map generated during act 109, as opposed to comparing calculated CC values to threshold CC values prior to CC map generation. In such instances, the process may continue to act 111 after completing act 109. For example, the system may compare correlation coefficients of corresponding portions of the CC map to a de-correlation threshold value (e.g., a de-correlation threshold value of 0.91, although other values are also envisioned and may be set and/or selected by the user and/or system as described above). For example, the system may determine whether the correlation coefficients of corresponding portions of the CC map are less than the de-correlation threshold value. Accordingly, if it is determined that the correlation coefficients of corresponding portions of the CC map are less than the de-correlation threshold value, the system may determine that the correlation coefficients and the corresponding portions of the CC map are de-correlated. Conversely, if it is determined that the correlation coefficients of corresponding portions of the CC map are not less than (e.g., equal to or greater than) the de-correlation threshold value, the system may determine that the correlation coefficients and the corresponding portions of the CC map are correlated. Then, the system may mark those portions of the CC map that were determined to be de-correlated as blood regions. Similarly, the system may mark those portions of the CC map that were determined to be correlated as non-blood regions (e.g., tissue regions). Generally, correlation may be indicative of portions of the CC map moving in unison and, de-correlation may be indicative of portions of the CC may not moving in unison. After completing act 111, the process may continue to act 113.

During act 113, the process may render the CC map on a rendering device of the system such as on a display of the system. Those areas of the CC map which may have been determined to be marked as a blood region may be highlighted for the convenience of the user, if desired. Further, the system may determine whether there are any marked blood regions (e.g., based upon the determination of act 111) and may generate a message to a user such as "warning: blood region detected" or the like and may render this message for the convenience of the user. Moreover this message may be associated with the detected blood region such as by superposing the message over the CC map at or near the marked blood region or by drawing a line and/or arrow between the message and the marked blood region. It is also envisioned that the system may draw a line (e.g., a circle, etc.) about the marked blood region, if desired. For example, the system may determine a blood region on the CC map and delineate this region (from a tissue region or regions) using any suitable method such as highlighting and/or dotted lines. In accordance with embodiments of the present system, the CC map may be rendered along a corresponding ultrasound map such as a B mode image map and/or other ultrasound images as may be selected by the user and/or system. This may provide a visual aid to a user (e.g., a clinician) which may help the user navigate a medical instrument, such as a catheter and/or an ultrasound probe capturing the ultrasound information. After completing act 113, the process may continue to act 115.

During act 115, the process may store information generated by the system in a memory of the system for later use and may continue to act 117, where it may end.

Figure 2:
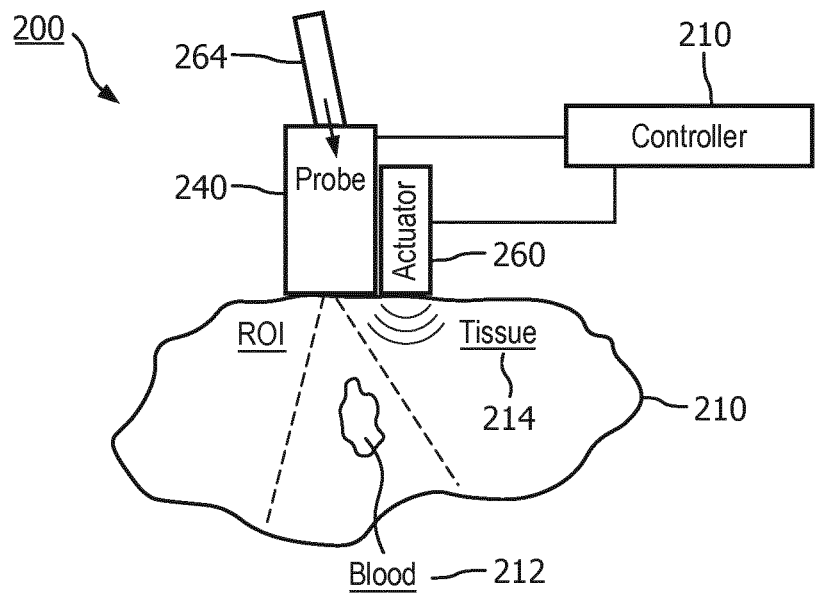
FIG. 2 shows a block diagram of a system operating in accordance with embodiments of the present system.

FIG. 2 shows a block diagram of a system 200 operating in accordance with embodiments of the present system. The system 200 may include one or more of a controller 210, a probe 240 such as an ultrasound transducer array, and an actuator 260. The controller 210 may control the overall operation of the system 200. For example, the controller 210 may be operative to drive the actuator 260 to emit a force sufficient to move tissue 214 in an ROI. Although the actuator 260 is shown to one side of the probe 240, the actuator 260 may include a plurality of actuators which may be situated on one or more sides of the probe 240. The controller 210 may drive the probe 240 to obtain ultrasound image information from the ROI. The controller 210 may then process the ultrasound image information to detect, for example, a blood pool such as blood 212 that may be interspersed within the tissue 214 of the ROI. In accordance with embodiments, it is envisioned that the actuator 260 may be mounted independently of, integrated with, or coupled to the probe 240. For example, in accordance with embodiments of the present system, the actuator 260 may be situated within a handle 264 of the probe 240 so as to impart a force to the probe 240 sufficient to move the tissue 214 within the ROI, as may be desired.

Figure 3:
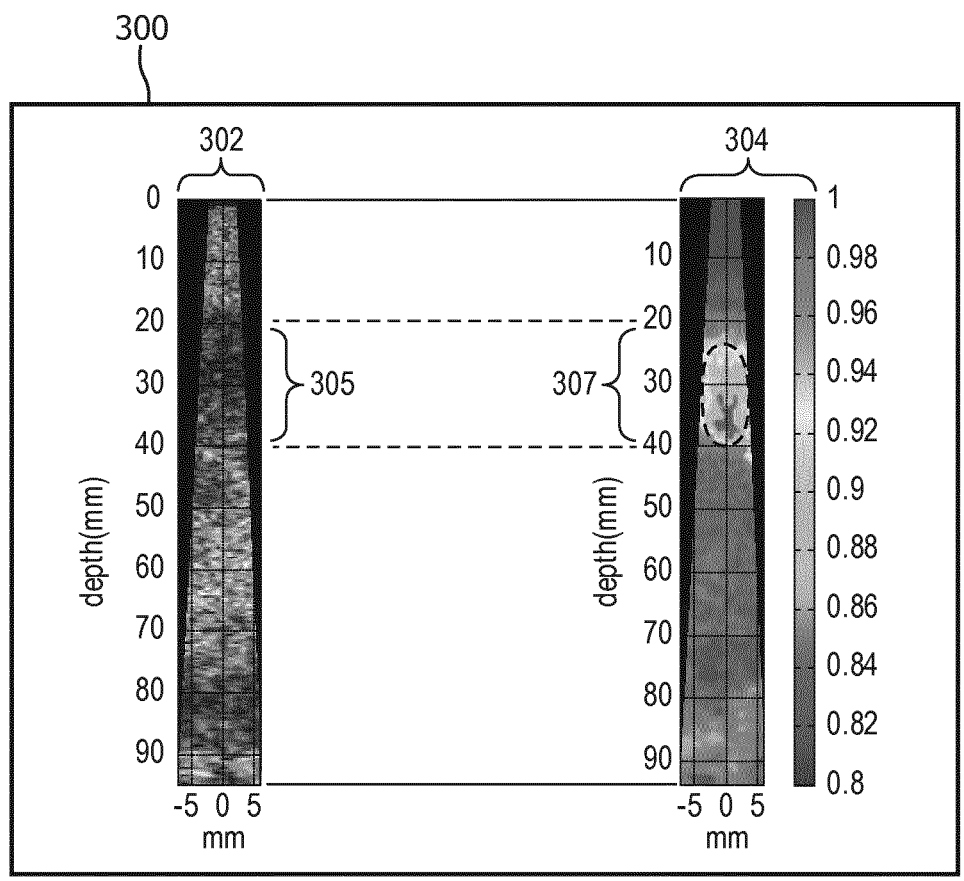
FIG. 3 shows a graph of blood de-correlated motion caused by motion due to breathing as determined by a BPD system operating in accordance with embodiments of the present system.

Examples of test results for first and second experiments obtained by embodiments of the present system will now be discussed with reference to FIGS. 3 and 4, respectively. More particularly, FIG. 3 shows a graph 300 of blood de-correlated motion caused by motion due to breathing as determined by an automated ultrasound blood pool detection (BPD) system operating in accordance with embodiments of the present system; and FIG. 4 shows a graph 400 of a phantom experiment illustrating blood de-correlated motion pattern caused by an external source such as hand tapping as determined by a BPD system operating in accordance with embodiments of the present system.

Referring to the first experiment (e.g., see FIG. 3), data was obtained using an animal study in which a number of RF datasets were collected from an animal (e.g., a pig, etc.) and processed in accordance with embodiments of the present system to investigate the blood motion caused by breathing movement of the animal. During this experiment, blood was harmlessly injected into the animal's abdomen and RF datasets were obtained (e.g., using an ultrasound probe) and processed. The blood can be seen in a B-mode image 302 from approximately 20 to 40 mm in depth as shown in a blood region 305. A correlation across two consecutive frames was calculated and is shown in a CC map 304 which illustrates de-correlation in a blood region 307 (which corresponds with the blood region 305). It is seen that solid tissue substantially in other depth ranges substantially outside of the blood region 307 moved more uniformly and maintained a relatively higher correlation between frames of the RF data set. The system may mark the de-correlated region(s) as shown by the dotted lines, if desired.

Figure 4:
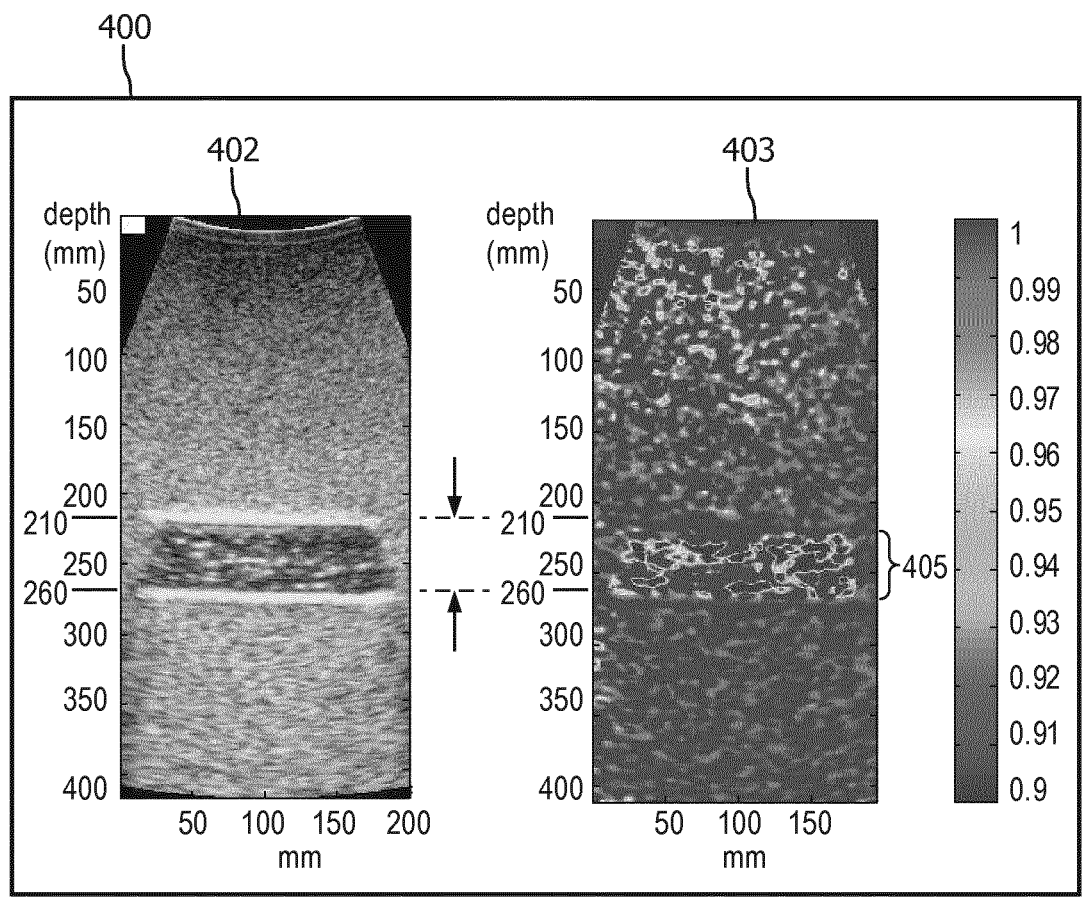
FIG. 4 shows a graph of a phantom experiment illustrating blood de-correlated motion pattern caused by an external source such as hand tapping as determined by a BPD system operating in accordance with embodiments of the present system.

Referring to the second experiment shown in FIG. 4, in this test, a channel was created inside tissue of a phantom. Then, blood mimicking fluid was poured inside of this channel. After a period of time had elapsed, the blood mimicking fluid became stationary and the test began. First, the phantom was tapped (to transfer a force to the phantom) from outside at a location that was near to a probe location, and DICOM data including DICOM video clips were acquired as the tapping continued. This tapping caused an external mechanical disturbance within the phantom and resulted in movement within both the phantom's tissue and the blood mimicking fluid situated within the channel. Referring to FIG. 4, the blood mimicking fluid can be seen in a B-mode image 402 from about 210 to 260 mm in depth. Analysis of a 2D correlation on the DICOM data was performed and a corresponding correlation graph 404 was generated. Blood containing regions were then distinguished from tissue. This correlation graph 404 and clearly shows a blood mimicking fluid region 405 has much more de-correlation than the solid phantom tissue situated about the blood mimicking fluid region 405. The system then formed a dotted line about the blood mimicking fluid regions 405 for the convenience of a user. This test establishes that the blood mimicking fluid has a more random motion pattern than the solid phantom tissue situated about it.

With reference to the methods used in the above-described examples, both of these methods do not require an acoustic radiation force to impart motion to the tissue and, thus, do not require high transmit power from an ultrasound system to detect blood pooling. Accordingly, embodiments of the present system may be used with regular imaging pulse sequence and/or data acquisition techniques and may be compatible with portable and/or ultra-mobile ultrasound platforms.

In operation, embodiments of the present system may: (a) focus upon differences in motion patterns such as differences in motion patterns between blood and soft tissue instead of differences in speed; and/or may (b) focus upon motion produced by different sources.

With respect to focusing on the differences in motion patterns such as differences in motion patterns between blood and soft tissue, for any given force, tissues are relatively more difficult to move blood, and tissues are more prone to return to their original position when the force is removed. Additionally, when under force, tissue tends to move in a uniform manner and maintains a high level of correlation to some extent. Blood, on the other hand, when subject to a force, undergoes relatively large displacement and does not return to its original configuration. Also, like any fluid, blood moves in a more random pattern than tissue and, therefore, loses correlation easily. Thus, by tracking these movements, determining de-correlation patterns with radiofrequency (RF) or image data, embodiments of the present system may identify and distinguish fluid regions from (surrounding) soft tissue.

With respect to motion produced by different sources, these sources may be characterized as internal and external sources.

Figure 5:
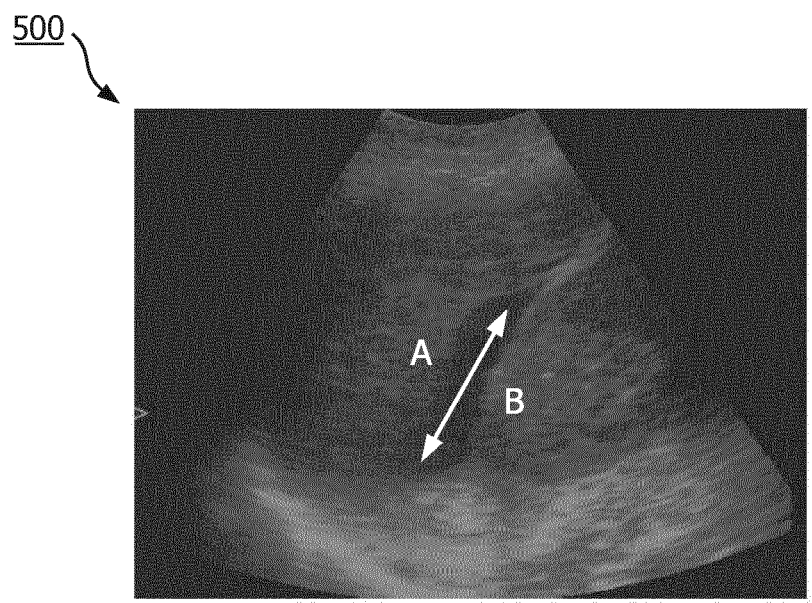
FIG. 5 shows an ultrasound B-mode image of fluid in Morrison's pouch situated between a patient's liver (A) and kidney (B)

Internal sources may include sources due to internal sources of a body of a subject under test such as a patient. The use of internal sources may be subject to location. For example, in a human a source of blood resides between internal organs such as in Morrison's porch between the liver and kidney as illustrated in FIG. 5 which shows an ultrasound B-mode image 500 of fluid in Morrison's pouch situated between a patient's liver (A) and kidney (B). As the organs within body move as part of body functions such as breathing, the organs push and/or squeeze the blood (such as the blood in Morrison's pouch).

External forces may include forces which are not due to forces originating within a body of a subject under test. For example, external forces may include forces due to a force generator such as an actuator coupled to the subject under test (e.g., a body of a patient). This force may produce movement in the tissue and blood of the subject under test and may be considered as a force outside a subject's body for producing movement. External forces may be generated by any suitable external force generator or generators such as mechanical actuators, solid-state actuators, and the like. Mechanical actuators may, without limitation, include motors, solenoids, and the like. However, it is also envisioned that external forces may be generated by low power ultrasound pulses from low power ultrasound transducers and which may be applied to a region of interest. These low power ultrasound pulses may enhance motion in the region of interest and may have lower amplitude and/or shorter pulse duration than pules produced by known acoustic streaming methods. As the above-described low power ultrasound pulses do not require much power to generate, they do not require a powerful transmit circuit ultrasound systems. Accordingly, these low power ultrasound pulses may be produced by portable and ultra-mobile systems and may easily satisfy expected acoustic safety guidelines.

Without limitation, it should be understood that in embodiments of the present system external forces may further be generated manually by an operator (e.g., a clinician, etc.) such as by gently tapping a ROI with any suitable object such as the hand and/or fingers of the user (e.g., the clinician) and/or by applying reciprocal motion to an ultrasound probes when it is coupled to the subject under test. Accordingly, embodiments of the system may incorporate sensors such as an accelerometers and/or pressure sensors whose sensor information may be analyzed by a controller of the system to detect the presence and/or absence of this reciprocal motion. Accordingly, if the absence of the reciprocal motion is detected, the system may inform a user so as to prevent erroneous results.

Accordingly, embodiments of the present system may provide a BPD system which may be operative with internal or external forces. For example, during normal breathing, forces sufficient to impart motion in a blood region of an ROI may be generated by organs and/or tissue of a subject under test. However, it is also envisioned that other methods of generating forces sufficient to impart motion in the blood region of the ROI may be generated by external sources such as by a clinician and/or by an actuator. These generated forces may be coupled to the ROI so that accurate BPD may occur.

Compared to acoustic streaming which requires a high power ultrasound probes, embodiments of the present system may adapt one or more low power motion sources. This may enhance portability, battery life, and workflow. Accordingly embodiments of the present system may be ideal for use with portable and/or ultra-mobile ultrasound platforms, where only limited ultrasound transmit power may be available. Additionally, since embodiments of the present system do not require a high intensity acoustic pulse, they may provide real-time detection and may be easier to fit into an expected fast workflow of emergency and/or ICU rooms.

Further, embodiments of the present system may employ low power imaging pulses and use RF or DICOM data to detect blood pooling in an ROI. As low power imaging pulses are used, embodiments of the present system may be particularly adaptable with many ultrasound systems, particularly portable or ultra-mobile ultrasound systems. Such systems according to the present embodiments are of great interest in point-of-care applications, especially for diagnosis and treatment of blunt abdominal trauma and chest trauma. The present systems may also be used in a variety of settings such as ambulance, emergency room, or critical care settings. However, it is also envisioned that embodiments of the present system may be suitable for field use in, for example, military and/or civilian casualty situations.

Although embodiments of the present system may have been described with reference to detecting blood pools in the abdomen, it should be appreciated that embodiments of the present system may, without limitation, be used for detecting blood pools in other areas of a body such as the flank, the pelvic area, the chest.

In accordance with embodiments of the present system blood pooling may be detected in real time using low power ultrasound methods.

Figure 6:
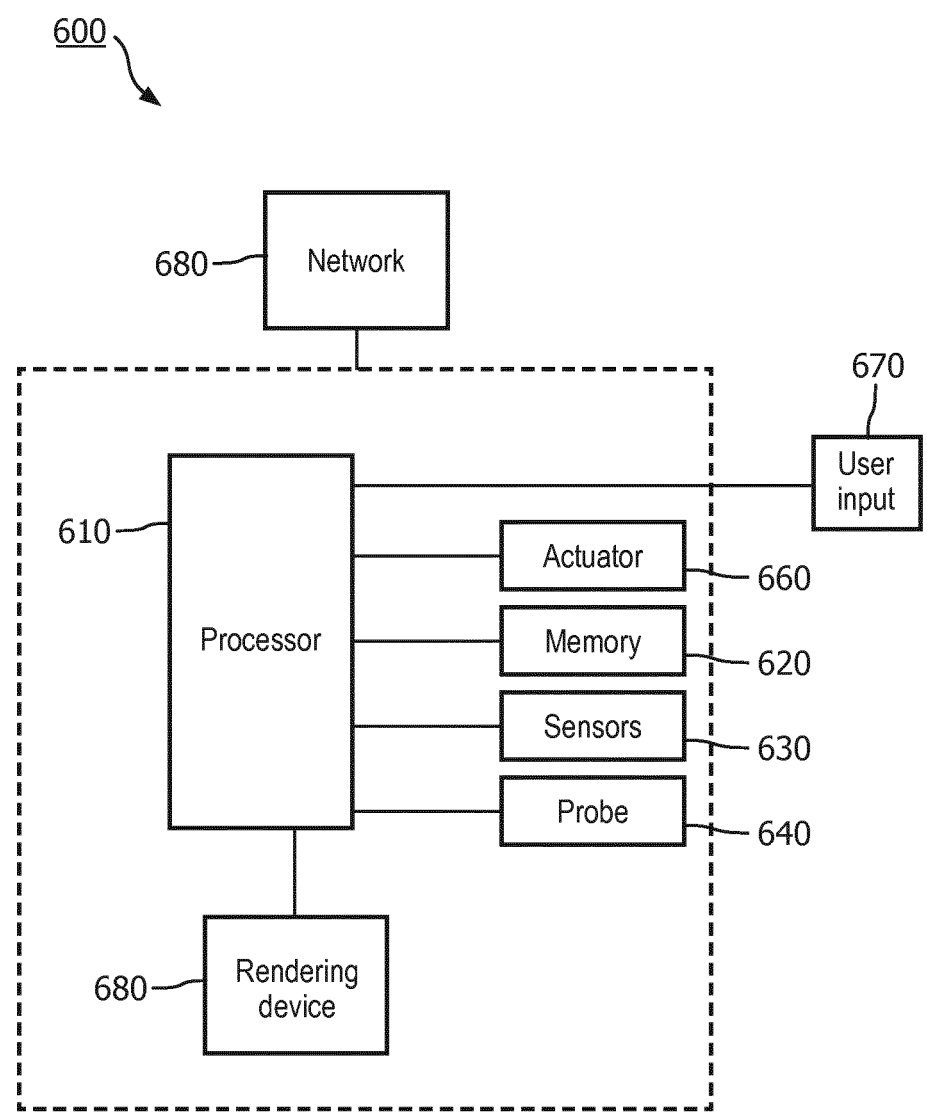
FIG. 6 shows a portion of a system in accordance with embodiments of the present system.

FIG. 6 shows a portion of a system 600 in accordance with embodiments of the present system. For example, a portion of the present system 600 may include a processor 610 (e.g., a controller) operationally coupled to a memory 620, a probe 640, sensors 630, an actuator 660, and a user input device 670. The memory 620 may be any type of device for storing application data as well as other data related to the described operation. The application data and other data are received by the processor 610 for configuring (e.g., programming) the processor 610 to perform operation acts in accordance with the present system. The processor 610 so configured becomes a special purpose machine particularly suited for performing in accordance with embodiments of the present system.

The operation acts may include configuring the system 600 by, for example, configuring the processor 610 to obtain information from user inputs, the probe 640, the sensors 630, and/or the memory 620 and processing this information in accordance with embodiments of the present system to obtain information related to an acquired image and which may form at least part of image information in accordance with embodiments of the present system. The user input portion 670 may include a keyboard, a mouse, a trackball and/or other device, including touch-sensitive displays, which may be stand alone or be a part of a system, such as part of a personal computer, a notebook computer, a netbook, a tablet, a smart phone, a personal digital assistant (PDA), a mobile phone, and/or other device for communicating with the processor 610 via any operable link. The user input portion 670 may be operable for interacting with the processor 610 including enabling interaction within a user interface (UI) as described herein. Clearly the processor 610, the memory 620, the UI 680 and/or user input device 670 may all or partly be a portion of a computer system or other device such as a client and/or server as described herein.

Operation acts may include requesting, providing, and/or rendering of information such as, for example, ultrasound image information of a volume in whole or part related to a subject under test such as a patient, a phantom, etc. The processor 610 may render the information on the UI 680 such as on a display and/or printer of the system. The probe 640 may include sensors such as ultrasound transducers in an array to provide desired sensor information to the processor 610 for further processing in accordance with embodiments of the present system.

The methods of the present system are particularly suited to be carried out by processor programmed by a computer software program, such program containing modules corresponding to one or more of the individual steps or acts described and/or envisioned by the present system.

The processor 610 is operable for providing control signals and/or performing operations in response to input signals from the user input device 670 as well as in response to other devices of a network and executing instructions stored in the memory 620. For example, the processors 610 may obtain feedback information from the sensors 630, the probe 640, etc., and may process this information to determine how to drive transducers of the probe 640 and/or actuator 660. The processor 610 may include one or more of a microprocessor, an application-specific or general-use integrated circuit(s), a logic device, etc. Further, the processor 610 may be a dedicated processor for performing in accordance with the present system or may be a general-purpose processor wherein only one of many functions operates for performing in accordance with the present system. The processor 610 may operate utilizing a program portion, multiple program segments, or may be a hardware device utilizing a dedicated or multi-purpose integrated circuit.

Embodiments of the present system employ inherent and/or external motion sources rather than acoustic streaming methods. It is envisioned that embodiments of the present system may expand the application of BPD to a wider range of pre-hospital settings where ultra-portable and/or mobile ultrasound platforms having limited power output power are used. For example, embodiments of the present system may be ideal for use during initial evaluation of a patient such as may occur in the field or in emergency rooms. Further, embodiments of the present system do not suffer from disadvantages of acoustic streaming systems such as high temperatures and required cool-down periods to maintain temperatures below spatial peak time average intensity at the focal spot ($I_{spta}$) limits.

Further, embodiments of the present system may take full advantage of ultra-portable or ultra-mobile ultrasound systems to obtain necessary ultrasound information, and assist less-trained users such as first responders and ambulance personnel to quickly and effectively detect blood pooling and other traumatic injuries. This may lead to faster triage, better patient care, and may enhance treatment outcome. Additionally, embodiments of the present system may improve workflow by reducing operator dependence, and may provide guidance for users such as care providers to determine when, for example, to perform surgery on a patient based on information provided by embodiments of the present system such as volume and rate of accumulation of a blood pool.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, any section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated;

i) the term "plurality of" an element includes two or more of the claimed element, and does not imply any particular range of number of elements; that is, a plurality of elements may be as few as two elements, and may include an immeasurable number of elements; and j) the term and/or and formatives thereof should be understood to mean that only one or more of the listed elements may need to be suitably present in the system in accordance with the claims recitation and in accordance with one or more embodiments of the present system.

What is claimed is:

1. An ultrasound imaging apparatus, comprising:
at least one controller configured to:
determine a location of an anatomical region of interest (ROI) and, responsive to determining the location, select one of two potential sources of push force for inclusion in a subsequent step of acquiring ultrasound image data, wherein the two potential sources of push force comprise (i) an internal source of push force and (ii) an external source of push force, wherein the internal source provides an internal push force originating from within the subject that induces movement within the ROI, and wherein the external source is configured to generate an external push force that comprises at least one low-enemy pulse generated by a low-energy actuator that, when externally applied to the subject, induces movement within the ROI, wherein the low-energy actuator is operative to generate low-energy pulses at a desired frequency and/or amplitude which is lower than high-energy pulses, generated via a high-energy actuator, at a respective frequency and/or amplitude required for acoustic streaming methods;
acquire ultrasound image data of the anatomical region-of-interest (ROI) in the subject to track induced movement across a period of time, the ultrasound image data comprising at least two frames acquired at different times as a push force induces movement within the anatomical ROI, wherein the push force comprises the internal push force or the external push force based on the determined location of the anatomical ROI;
determine a correlation between the at least two frames and form corresponding correlation coefficients;
generate a correlation coefficient (CC) map based upon the acquired ultrasound image data and information of the determined correlation between the at least two frames, wherein the CC map indicates different extents of correlation and de-correlation between fluids and surrounding tissues;
distinguish fluid from tissue within the CC map based upon a comparison of the correlation coefficients with at least one threshold value of correlation coefficients for tissues, fluids, and/or indeterminable objects, wherein the indeterminable objects have a correlation coefficient threshold value between fluid and tissue coefficient threshold values; and
highlight one or more portions of the CC map determined to be at least fluid.

2. The apparatus of claim 1, wherein during the comparison the at least one controller determines whether the correlation coefficients are less than a threshold value.

3. The apparatus of claim 2, wherein when the correlation coefficients are determined to be less than the threshold value, the at least one controller marks a corresponding area on the CC map as a fluid area.

4. The apparatus of claim 2, wherein when the correlation coefficients are determined to be not less than the threshold value, the at least one controller marks a corresponding area on the CC map as a tissue area.

5. A method of displaying ultrasound images, the method performed by at least one controller of an imaging system and comprising acts of:
determining a location of an anatomical region of interest (ROI) and selecting in response to the determined location one of two potential sources of push force for inclusion in a subsequent step of acquiring ultrasound image data, wherein the two potential sources of push force comprise (i) an internal source of push force and (ii) an external source of push force, wherein the internal source provides an internal push force originating from within the subject that induces movement within the ROI, and wherein the external source is configured to generate an external push force that comprises at least one low-energy pulse generated by a low-energy actuator that, when externally applied to the subject, induces movement within the ROI, wherein the low-energy actuator is operative to generate low-energy pulses at a desired frequency and/or amplitude which is lower than high-energy pulses, generated via a high-energy actuator, at a respective frequency and/or amplitude required for acoustic streaming methods;
acquiring ultrasound image data of the anatomical region-of-interest (ROI) of the subject to track induced movement across an interval of time, the ultrasound image data comprising at least two frames acquired at different times over the interval of time as a push force induces movement in the anatomical ROI, wherein the push force comprises the internal push force or the external push force based on the determined location of the anatomical ROI;
determining a correlation between the at least two frames and forming corresponding correlation coefficients;

generating a correlation coefficient (CC) map based upon the acquired ultrasound image data and information of the determined correlation between the at least two frames, wherein the CC map indicates different extents of correlation and de-correlation between fluids and surrounding tissues;

distinguishing fluid from tissue within the CC map based upon a comparison of the correlation coefficients with at least one threshold value of correlation coefficients for tissues, fluids, and/or indeterminable objects, wherein the indeterminable objects have a correlation coefficient threshold value between fluid and tissue coefficient threshold values; and highlighting one or more portions of the CC map determined to be at least fluid.

6. The method of claim 5, further comprising an act of determining whether the correlation coefficients are less than a threshold value based on the comparison.

7. The method of claim 6, further comprising an act of marking a corresponding area on the CC map as a fluid area when the correlation coefficients are determined to be less than the threshold value.

8. The method of claim 6, further comprising an act of marking a corresponding area on the CC map as a tissue area when the correlation coefficients are determined to be not less than the threshold value.

9. A non-transitory computer readable medium comprising computer instructions which, when executed by a processor, configure the processor to perform the acts of:

determining a location of an anatomical region of interest (ROI) and selecting in response to the determined location one of two potential sources of push force for inclusion in a subsequent step of acquiring ultrasound image data, wherein the two potential sources of push force comprise (i) an internal source of push force and (ii) an external source of push force, wherein the internal source provides an internal push force originating from within the subject that induces movement within the ROI, and wherein the external source is configured to generate an external push force that comprises at least one low-energy pulse generated by a low-energy actuator that, when externally applied to the subject, induces movement within the ROI, wherein the low-energy actuator is operative to generate low-energy pulses at a desired frequency and/or amplitude which is lower than high-energy pulses, generated via a high-energy actuator, at a respective frequency and/or amplitude required for acoustic streaming methods;

acquiring ultrasound image data of the anatomical region-of-interest (ROI) to track induced movement across an interval of time, the ultrasound image data comprising at least two frames acquired at different times over the interval of time as a push force induces movement within the anatomical ROI, wherein the push force comprises the internal push force or the external push force based on the determined location of the anatomical ROI;

determining a correlation between the at least two frames and forming corresponding correlation coefficients;

generating a correlation coefficient (CC) map based upon the acquired ultrasound image data and information of the determined correlation between the at least two frames, wherein the CC map indicates different extents of correlation and de-correlation between fluids and surrounding tissues;

distinguishing fluid from tissue within the CC map based upon a comparison of the correlation coefficients with at least one threshold value of correlation coefficients for tissues, fluids, and/or indeterminable objects, wherein the indeterminable objects have a correlation coefficient threshold value between fluid and tissue coefficient threshold values; and highlighting one or more portions of the CC map determined to be at least fluid.

10. The non-transitory computer readable medium of claim 9, wherein the computer instructions which, when executed by a processor, further configure the processor to perform an act of determining whether the correlation coefficients are less than a threshold value based on the comparison.

11. The non-transitory computer readable medium of claim 10, wherein the computer instructions which, when executed by a processor, further configure the processor to perform an act of marking a corresponding area on the CC map as a fluid area when the correlation coefficients are determined to be less than the threshold value.

12. The non-transitory computer readable medium of claim 10, wherein the computer instructions which, when executed by a processor, further configure the processor to perform an act of marking a corresponding area on the CC map as a tissue area when the correlation coefficients are determined to be not less than the threshold value.

13. The non-transitory computer readable medium of claim 9, wherein the computer instructions which, when executed by a processor, further configure the processor to perform an act of generating a push force to be coupled to the anatomical ROI.

14. The apparatus of claim 1, further comprising:
the low-energy actuator operative to generate low-energy pulses at the desired frequency and/or amplitude which is lower than high-energy pulses, generated via a high-energy actuator, at a respective frequency and/or amplitude required for acoustic streaming methods.

15. The apparatus of claim 14, wherein responsive to a selection of the potential source of push force being the external source of push force, the at least one controller is further configured to drive the low-energy actuator to generate the low-energy pulses for being externally applied to the subject.

16. The apparatus of claim 1, wherein the at least one controller is configured to determine the location of the anatomical ROI by identifying one or more of (i) a type of scan selected for acquiring the ultrasound image data, and (ii) a user selection of the external source rather than the internal source.

17. The method of claim 5, further comprising:
generating, via the low-energy actuator, low-energy pulses at the desired frequency and/or amplitude which is lower than high-energy pulses, generated via a high-energy actuator, at a respective frequency and/or amplitude required for acoustic streaming methods, wherein the generating is in response to a selection of the potential source of push force being the external source of push force, via the at least one controller, and driving the low-energy actuator, via the at least one controller, to generate the low-energy pulses for being externally applied to the subject.

18. The method of claim 5, further comprising:
rendering, via the at least one controller, the CC map along with a corresponding ultrasound image on a display device as a visual aid for assisting with a navigation of a medical instrument and/or an ultrasound probe capturing ultrasound information.

19. The method of claim 5, wherein determining the location of the anatomical ROI, via the at least one controller, further comprises identifying one or more of (i) a type of scan selected for acquiring the ultrasound image data, and (ii) a user selection of the external source rather than the internal source.

20. The apparatus of claim 1, wherein the at least one controller is further configured to render the CC map along with a corresponding ultrasound image on a display device as a visual aid for assisting with a navigation of a medical instrument and/or an ultrasound probe capturing ultrasound information.

\* \* \* \* \*